United States Patent [19]

Godley, III et al.

[11] Patent Number: 5,306,298
[45] Date of Patent: Apr. 26, 1994

[54] ADJUSTABLE LARYNGOPLASTY DEVICE

[76] Inventors: Frederick A. Godley, III, Four Rogers Ave., North Kingstown, R.I. 02852; Paul C. Christu, 174 Church St., East Greenwich, R.I. 02818

[21] Appl. No.: 18,294

[22] Filed: Feb. 16, 1993

[51] Int. Cl.[5] ............................................. A61F 2/20
[52] U.S. Cl. ........................................ 623/9; 623/11
[58] Field of Search ................ 600/23, 24; 623/9, 14, 623/11

[56] References Cited

U.S. PATENT DOCUMENTS

| | | | |
|---|---|---|---|
| 4,198,542 | 4/1980 | Ducommun | 128/905 X |
| 5,197,982 | 3/1993 | Goldsmith et al. | 623/9 |
| 5,201,765 | 4/1993 | Netterville et al. | 623/11 |

FOREIGN PATENT DOCUMENTS 0453186  10/1991  European Pat. Off. ............... 623/9

*Primary Examiner*—Randall L. Green
*Assistant Examiner*—D. Willse
*Attorney, Agent, or Firm*—Salter, Michaelson & Benson

[57] ABSTRACT

An adjustable laryngoplasty device is provided for medializing a paralyzed vocal cord in a larynx. The device includes an anchoring plate, a prosthesis member, and a pair of adjustment screws which are threaded through the anchoring plate and rotatably connected to the prosthesis member. A window is formed in the patient's thyroid cartilage adjacent the paralyzed vocal cord and the prosthesis member is extended through the window so that it presses against the underlying vocal cord. The anchoring plate is secured to the outer surface of the thyroid cartilage with self-tapping screws which are extended through apertures in the anchoring plate and imbedded into the thyroid cartilage. The adjustment screws are rotatable for moving the prosthesis member relative to the anchoring plate and thereby adjusting the medial position of the vocal cord in the larynx.

20 Claims, 2 Drawing Sheets

ADJUSTABLE LARYNGOPLASTY DEVICE

BACKGROUND OF THE INVENTION

The instant invention relates to surgical devices and more particularly to a surgical device for use in the treatment of unilateral vocal cord paralysis.

Unilateral vocal cord paralysis is a relatively common disorder in which one of the two vocal cords becomes paralyzed. Such paralysis most often occurs when the recurrent laryngeal nerve on one side of the neck is injured by surgery, trauma or a tumor. When the laryngeal nerve is damaged, the associated vocal cord no longer functions normally, and it rests flaccidly to the side of the larynx. The remaining vocal cord is functional. However it cannot cross over the mid-line of the larynx to press against the paralyzed vocal cord and form sounds properly, and therefore these patients have a hoarse breathy voice, have difficulty raising their voices or coughing, and often aspirate fluids when swallowing.

It has been found that unilateral vocal cord paralysis can be corrected by artificially moving the paralyzed vocal cord toward the mid-line of the larynx where the functional vocal cord can press against it. One known treatment for manipulation of the paralyzed vocal cord comprises injecting the paralyzed vocal cord with aliquots of TEFLON (registered TM of Dupont) paste which effectively expand the vocal cord toward the mid-line of the larynx. A surgical procedure has also been developed wherein the surgeon approaches the patient's thyroid cartilage externally, and cuts a small rectangular window in the thyroid cartilage to create a rectangular panel of cartilage adjacent to the paralyzed vocal cord. Theoretically the cartilage remnant reduces the risk of erosion of the prosthesis, but the reported experience of surgeons who remove the cartilage is that there have been no complications and that the surgeons believe that the vocal quality of the patients is improved with this technique. In either case, the soft tissue, including the paralyzed vocal cord, can then be pressed into the laryngeal airway until the patient can phonate optimally. In the existing technique a silastic shim is then estimated in size and shape and cut to fill the window and to hold the soft tissue and vocal cord in position. The block is then secured to the thyroid cartilage with sutures or flanges.

The technique of vocal medialization with a silastic shim has two clear advantages over the TEFLON paste injections. First, the silastic prosthesis can be removed and replaced with a different size prosthesis if airway or vocal cord problems occur. Second, the silastic implant also avoids the migration of Teflon paste or the formation of granulation tissue.

The major drawback to both of these procedures is that they are not easily adjusted to the individual dimensions of each patient's larynx. In other words, it is difficult to fine-tune the patient's optimal voice with either of these techniques. On the one hand, the Teflon technique makes it difficult to estimate the exact amount and location of each aliquot of paste. On the other hand, it is difficult to customize the shape of the silastic block during the surgical procedure. There has also been described an adjustable medialization technique which relies on an implanted balloon, but the theoretically less precise expansion of a balloon and risk of leakage make this alternate technique potentially less attractive.

SUMMARY OF THE INVENTION

The instant invention provides an adjustable laryngoplasty device for medializing a paralyzed vocal cord in a larynx.

Briefly, the device comprises a rectangular anchoring plate, a prosthesis member, and a pair of adjustment screws which threadedly engage a pair of threaded apertures in the anchoring plate and are rotatably connected to the prosthesis member. In a first embodiment, the prosthesis member comprises a wedge-shaped block, and in further embodiments the prosthesis member comprises a rectangular plate element. A rectangular window is cut in the patient's thyroid cartilage to form a rectangular panel of cartilage adjacent to the paralyzed vocal cord. The cartilage panel is pushed inwardly, and the prosthesis is inserted through the window so that it presses against the cartilage panel, and the underlying soft tissues, including the paralyzed vocal cord. The anchoring plate is received against the outer surface of the thyroid cartilage, and it is secured thereto by self-tapping screws which are extended through apertures at each end of the anchoring plate and secured into guide holes formed in the thyroid cartilage. The adjustment screws are rotatable in their threaded apertures, and they are operative for adjustably moving the prosthesis member relative to the fixed anchoring plate. The prosthesis member pushes against the cartilage panel, underlying soft tissues, and vocal cord, thereby repositioning the paralyzed vocal cord near the midline of the larynx. The prosthesis can be adjusted and readjusted very easily without having to be removed.

Accordingly, it is an object of the instant invention to provide a laryngoplasty device for medializing a paralyzed vocal cord in a patient's larynx.

It is another object to provide a pre-formed, single-sized adjustable laryngoplasty device for adjustably positioning a paralyzed vocal cord in a patient's larynx.

It is still another object to provide a surgical device which is readily adjustable and securable to the patient's thyroid cartilage.

It is yet another object to provide a laryngoplasty device which can be adjusted and readjusted without having to be removed, if vocal cord innervation returns after several months or years, then the device could be removed.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE PREFERRED EMBODIMENTS

Figure 1:
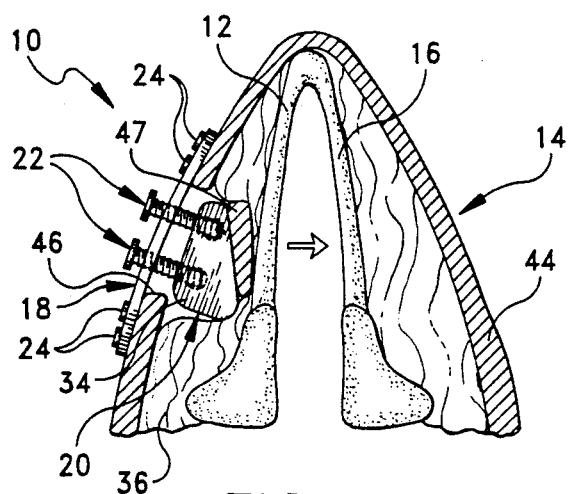
FIG. 1 is a cross sectional view of a human larynx with the adjustable laryngoplasty device of the instant invention inserted through a rectangular window formed in the patient's thyroid cartilage.
Figure 2:
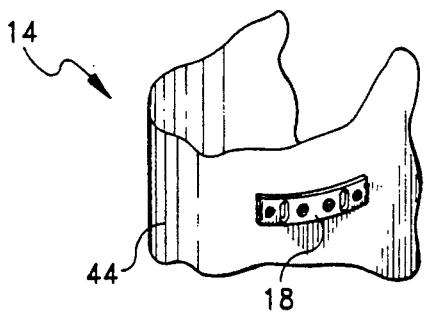
FIG. 2 is a perspective view thereof.
Figure 3:
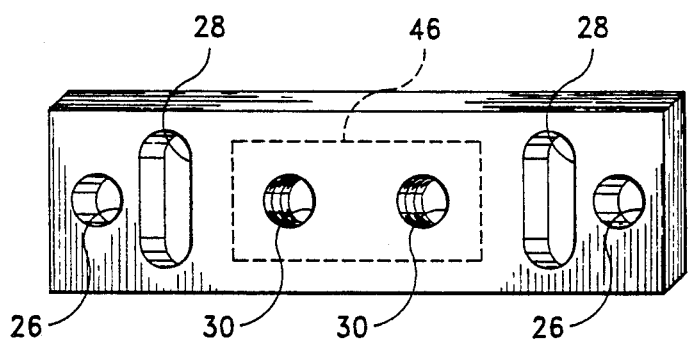
FIG. 3 is an enlarged perspective view of the anchoring plate which forms a part of the device.
Figure 4:
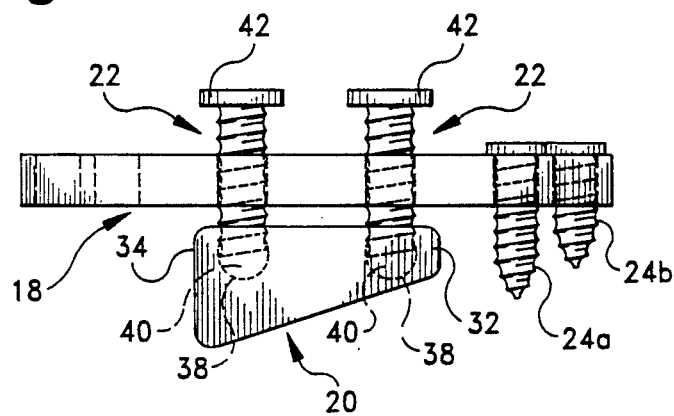
FIG. 4 is an elevational view of the anchoring plate with the prosthesis member, adjustment screws and attachment screws assembled therewith.

Referring now to the drawings, a first embodiment of the adjustable laryngoplasty device of the instant invention is illustrated and generally indicated at 10 in FIGS. 1 through 4. As will hereinafter be more fully described, the device 10 is operative for medializing a paralyzed vocal cord 12 in a patient's larynx generally indicated at 14 so that the remaining functional vocal cord 16 can press against the paralyzed vocal cord 12. The device 10 comprises an anchoring plate generally indicated at 18, a prosthesis member generally indicated at 20, a pair of adjustment screws generally indicated at 22 and a plurality of attachment screws 24.

The anchoring plate 18 is preferably rectangular in geometry and it is preferably formed from vitallium or titanium, although other similar bio-compatible metal alloys or plastics are also suitable. The rectangular anchoring plate 18 is preferably 6 mm wide, 24 mm long, and 2 mm thick, although other dimensions are permissible within the scope of the invention. The anchoring plate 18 includes a pair of apertures 26 which are respectively formed therein adjacent to the opposite ends of the plate 18, a pair of slots 28 which are respectively formed therein adjacent to the apertures 26, and a pair of closely spaced, threaded apertures 30 formed in the plate 18 between the slots 28. The design of the anchoring plate allows horizontal (anterior-posterior) and vertical (caudal-cephalic) adjustment of the anchoring plate with the two non-threaded screw apertures 26 and two non-threaded slots 28. Specifically, the slots 28 allow the vertical adjustment of the anchoring plate if the rectangular cartilage window is not exactly cut at the level of the paralyzed vocal cord. The non-threaded screw apertures 26 serves three potential purposes. First they can be used if the anchoring plate needs to be moved anteriorly or posteriorly after the drill holes have already been drilled in the wrong place for slots 28. Secondly, if the threads of the slot 28 screws do not hold well in the cartilage, the apertures 26 are available for a screw. Thirdly, apertures 26 can be used in addition to slots 28 to secure the anchoring plate more reliably to the thyroid cartilage.

The prosthesis member 20 is preferably formed from a metal or plastic or ceramic material and it is generally wedge-shaped in construction but may be flat. The prosthesis member 20 is preferably 4 mm wide and 10 mm long, and it has an anterior end 32 which is preferably 2 mm thick, and a posterior end 34 which is preferably 5 mm thick. It is pointed out that the posterior end 34 of the prosthesis member 20 is thicker than the anterior end 32 because the soft tissues 36 in the posterior portion of the larynx 14 are thicker than in the anterior portion, and therefore they must be medially displaced a greater distance in order to properly position the vocal cord 12 along the midline of the larynx 14 (See FIG. 1). The prosthesis member 20 further includes a pair of sockets 38 (shown in broken lines) which are adapted to receive the adjustment screws 22.

The adjustment screws 22 are preferably 2 mm in diameter and 7 mm in length, and they each include a ball element 40 (shown in broken lines) at a first end thereof and a head portion 42 at a second end thereof. The adjustment screws 22 are threaded through the threaded apertures 30 in the anchoring plate 18 and the ball elements 40 are received into the sockets 38 in the prosthesis member 20 to form a ball and socket joint. The adjustment screws 22 threadedly engage the threaded apertures 30, and in this regard, they are operable for adjustably moving the prosthesis member 20 relative to the anchoring plate 18. It is pointed out that the ball 40 and socket 38 joints enable the adjustment screws 22 to rotate relative to the prosthesis member 20 when the screws 22 are rotated in the threaded apertures 30 and it is also pointed out that the ball 40 and socket 38 joints enable the prosthesis member 20 to pivot with respect to each adjustment screw 22 so that one adjustment screw 22 may be extended further than the other. The head portions 42 of the adjustment screws 22 include socket means (not shown), such as a slot, which are adapted to receive an adjustment tool, such as a screw driver or the like, for rotating the screws 22. There are other potential mechanical means to securely join the adjustment screws 22 and the prosthesis member 20.

The attachment screws 24 preferably comprise self-tapping surgical screws which are suitable for being secured into human cartilage. The self-tapping screws 24 are preferably 2 mm in diameter and 4-6 mm in length.

For implantation of the device 10, the patient is given intravenous sedation and local anesthesia, and a 4-5 cm horizontal incision is made in the neck on the side of the paralyzed vocal cord 12. The strap muscles (not shown) are separated to reveal the thyroid cartilage 44 and a rectangular window 46 is then cut in the thyroid cartilage 44 to form a rectangular panel of cartilage 47 adjacent to the paralyzed vocal cord 12. As stated previously in the Background portion of this specification, the cartilage panel 47 remains attached to the underlying soft tissue 36 and, in general, does not need to be removed. The rectangular window 46 is preferably 10 mm wide by 4 mm in height, but the window 46 can be formed slightly larger or smaller according to the sex of the patient and the preference of the surgeon. The thyroid cartilage 44 is preferably cut with a scalpel, although a reciprocating saw or fine drill may be used depending on the level of calcification. The cartilage panel 47 is pushed inwardly, and then the prosthesis 20 is inserted through the window 46 so that the posterior end 34 thereof is positioned toward the posterior of the larynx 14. The prosthesis member 20 presses against the cartilage panel 47 and underlying soft tissues 36, including the paralyzed vocal cord 12, to push the paralyzed vocal cord 12 towards the midline of the larynx 14. The anchoring plate 18 is received against the outer surface of the thyroid cartilage 44 and then secured to the thyroid cartilage 44 with the self-tapping screws 24 which are extended through the apertures 26 and slots 28 in the anchoring plate, and threaded into guide holes (not shown) which are formed in the thyroid cartilage 44. Preferably, two 6 mm screws 24a (FIG. 4) are secured in the thyroid cartilage 4 through the slots 28 so that the anchoring plate 18 can be slidably adjusted to the correct position, and then two 4 mm screws 24b (FIG. 4) are secured in the cartilage 44 through the apertures 26 to hold the plate 18 in the desired position. The choice of screw length is dependent upon the thickness of the underlying cartilage, and the preference of the surgeon, it being pointed out that the longer screws 24a have better holding strength than the shorter screws 24b. The guide holes for the screws 24 are preferably formed with a perforating drill, although for application of the screws 24 in calcified or brittle cartilage, a 1 mm diamond otologic bur should be used instead of a perforating drill. The bur preserves the inner thyroid perichondrium from injury. In soft cartilage, the guide holes can effectively be formed with a 22-gauge needle, rather than a drill. It is pointed out that with softer cartilage, the screws 24 must be applied with great care to avoid stripping from overtightening.

The prosthesis member 20 is then adjusted medially by rotating the adjustment screws 22 to move the prosthesis 20 toward or away from the anchoring plate 18. As explained previously, the prosthesis member 20 pushes against the panel of cartilage 47 and the underlying soft tissues 36 so that the paralyzed vocal cord 12 is repositioned near the midline of the larynx 14. The proper degree of medialization is established when the vocalization and phonation time of the sedated patient ar optimized. The alternative embodiments 48, 52, 55, 70, and 82 are characterized by different designs of the anchoring plate 18, 56, 76, 88 and prosthesis member 50. The anchoring plates 56 and 76 feature flanges 68 and 78 which would make insertion of the anchoring plate potentially easier to use. There are three possible reasons that this modification may be useful. First, since there is limited stress on the anchoring plate, it is possible that a single or double screw on the anterior end of the anchoring plate might be all that is needed. Secondly, this anchoring plate design is a potential solution to the problem when it is difficult to secure a posterior screw on the anchoring plate. Thirdly, this flange might also make the insertion of the implant a quicker, simpler procedure.

The embodiments 52, 55, 70 and 82 also feature a portion of the anchoring plate 54, 66, 72 and 84 which fills the empty space in the cartilage window. This design offers two potential advantages. First, it is a theoretical biological advantage to fill this potential space with an inert material, rather than blood which might become infected in the immediate postoperative period or the scar tissue which would eventually replace the blood and thereby make it more difficult to remove the prosthesis. Secondly, this anchoring plate design modification might have an engineering advantage because there would be a greater thickness of material to hold a screw thread.

Most silastic block implants are shaped as a wedge because it conforms best to the shape of the larynx. The thyroid cartilage which surrounds the larynx is a broad curved V-shape when looked at in the horizontal plane. The vocal cords form a more acute V-shape. To medially displace a paralyzed vocal cord so that it rests evenly in the midline, the posterior soft tissues of the vocal cord have to be displaced more than the anterior portion. At this time the wedge shape of the silastic block technique is the common solution to this problem. It is possible that, with experience, this problem could be solved with prosthesis member 50 shaped as a flat plate which could be tilted at the proper angle with variable positions of adjustment screws 22. Alternative shapes of the prosthesis would also be compatible with this design.

Figure 5:
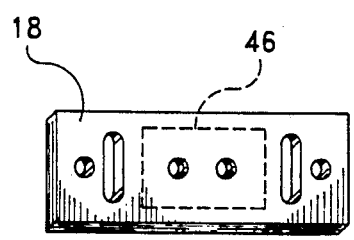
FIGS. 5 and 6 are perspective and elevational views of an alternative embodiment of the device.
Figure 6:
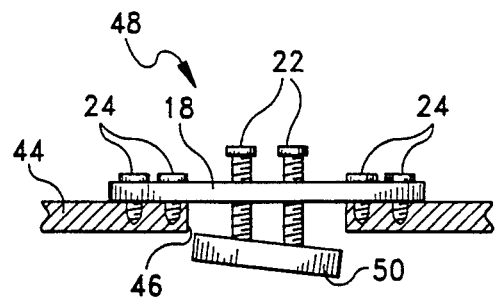

A second embodiment of the device is illustrated in FIGS. 5 and 6, and it is generally indicated at 48 in FIG. 6. In the second embodiment 48, the anchoring plate 18 remains the same, however, the prosthesis member comprises a rectangular plate element 50 with two sockets (not shown) formed therein. The ball elements 40 of the adjustment screws 22 are mounted in the sockets as described in the previous embodiment. It is pointed out that the plate element 50 is disposed at an angle to the anchoring plate 18 to mimic the wedge-shaped geometry achieved with the wedge-shaped prosthesis member 20. The embodiment 48 is secured and adjusted in the same manner as the first embodiment 10, and it is identical in all other respects.

Figure 7:
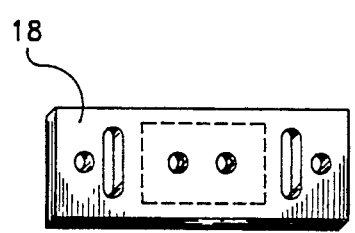
FIGS. 7 and 8 are similar views of a third embodiment of the device.
Figure 8:
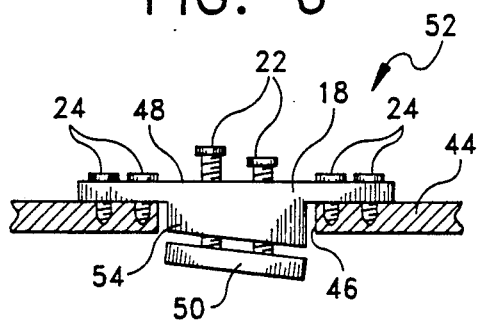

A third embodiment of the device is illustrated in FIGS. 7 and 8, and it is generally indicated at 52 in FIG. 8. In this third embodiment 52, the anchoring plate 18 includes a wedge-shaped body portion 54 which projects outwardly from the plate 18. The threaded apertures 30 extend through the body portion 54 and the prosthetic plate element 50 is connected to the adjustment screws 22 so that it lies adjacent to the body portion 54. The wedge-shaped body portion 54 is proportionally dimensioned so that it may be received through the window 46 in the thyroid cartilage 44 as illustrated in FIG. 8.

Figure 9:
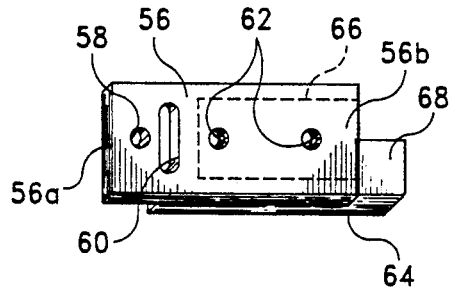
FIGS. 9 and 10 are similar views of a fourth embodiment thereof.
Figure 10:
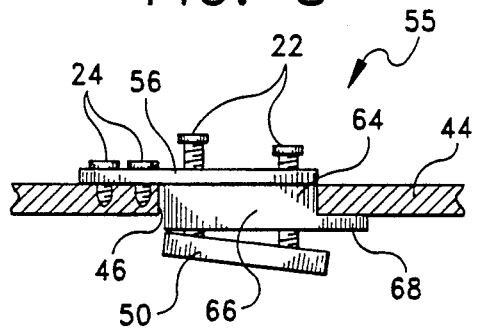

FIGS. 9 and 10 illustrate a fourth embodiment of the device which is generally indicated at 55. This embodiment 55 includes an anchoring plate 56 having first and second ends 56a and 56b, respectively, an aperture 58 formed adjacent to the first end 56a, a slot 60 formed adjacent to the aperture 58, and a pair of spaced, threaded apertures 62. The anchoring plate 56 further includes a flange member generally indicated at 64 comprising a body portion 66 which is secured to the anchoring plate 56 adjacent to the second end 56b, and a flange portion 68 which extends outwardly from the body portion 66 beyond the second end 56b of the anchoring plate 56. The threaded apertures 62 extend through the body portion 66 of the flange member 64. The adjustment screws 22 are extended through the threaded apertures 62 and the prosthetic plate element 50 is mounted to the adjustment screws 22 adjacent the body portion 66 of the flange member 64. This embodiment 55 of the device differs from previous embodiments in that the flange member 64 and prosthesis 50 are inserted through the window 46 in the cartilage with the flange portion 68 of the flange member 64 received against an inner surface of the thyroid cartilage 44 to further enhance connection of the assembly 55 to the cartilage. A pair of self-tapping screws 24 are then secured through the aperture 58 and slot 60 in the plate 56 to secure the device 55 to cartilage 44.

Figure 11:
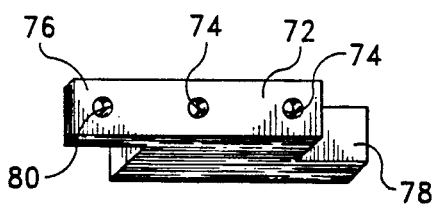
FIGS. 11 and 12 are similar views of yet another embodiment.
Figure 12:
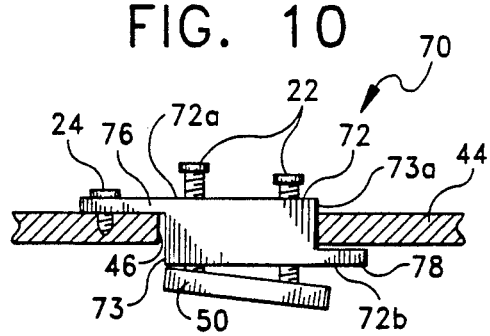

FIGS. 11 and 12 illustrate a fifth embodiment of the device which is generally indicated at 70 in FIG. 12. The fifth embodiment 70 comprises a body portion 72 having upper and lower surfaces 72a and b, first and second ends 73 and 73a, and a pair of threaded apertures 74 extending through the body portion 72. A first flange member 76 extends outwardly from the first end 73 of the body portion 72 adjacent to the upper surface 72a thereof and a second flange member 78 extends outwardly from the second end 73a of the body portion adjacent the lower surface 72b thereof. An aperture 80 is formed in the first flange member 76, and the prosthesis element 50 is connected to the adjustment screws 22 which threadedly pass through apertures 74. The second flange member 78 and body portion 72 are inserted through the window 46 in the cartilage 44 wherein the prosthesis presses against the cartilage panel 47, and the second flange member 78 is received adjacent the inner surface of the thyroid cartilage 44, while the first flange member 76 bears against the outer surface of cartilage 44, thus providing additional support for the mounting of body portion 72 relative to cartilage 44. A self-tapping screw 24 is extended through the aperture 80 in the first flange member 76 and secured in the thyroid cartilage 44.

Figure 13:
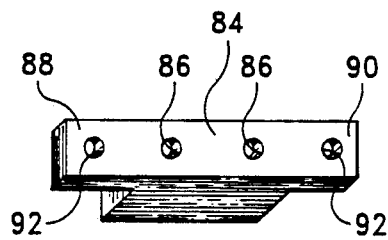
FIGS. 13 and 14 are similar views of still another embodiment.
Figure 14:
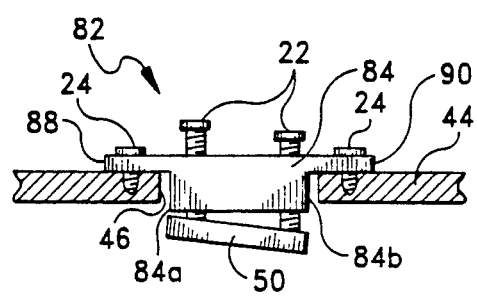

FIGS. 13 and 14 illustrate still another embodiment of the device which is generally indicated at 82. This sixth embodiment 82 comprises a body portion 84 having first and second ends 84a and 84b, and a pair of threaded apertures 86 extending through the body portion 84. First and second flange members 88 and 90 respectively, extend outwardly from the first and second ends of the body portion and an aperture 92 is formed in each flange member 88 and 90. The body portion 84 is extended through the window 46 in the cartilage 44 so that the prosthetic plate element 50 presses against the cartilage panel 47 and the flange members 88 and 90 are received against the outer surface of the cartilage 44. Self-tapping screws 24 are inserted through the apertures 92 in the flanges 88 and 90 and secured into the thyroid cartilage 44.

It is seen therefore that the instant invention provides an effective adjustable laryngoplasty device for medializing a paralyzed vocal cord 12 in a larynx 14. In each embodiment of the device, an anchoring portion is securely attached to the thyroid cartilage 44 while an adjustable prosthetic member 20 is extended through a window 46 formed in the thyroid cartilage 44 adjacent to the paralyzed vocal cord 12. A pair of adjustment screws 22 are extended through threaded apertures in the device and the adjustment screws 22 are rotatably connected to the prosthesis 20 so that the prosthesis 20 is movable relative to the anchoring portion. The prosthesis 20 presses against the panel of cartilage 47, and the underlying soft tissues 36 including the paralyzed vocal cord 12, so that the vocal cord 12 may be repositioned near the midline of the larynx 14. The adjustment screws 22 are effective for adjustably moving the prosthesis 20 and vocal cord 12 so that a proper degree of medialization can be achieved quickly and accurately. For these reasons, the device of the instant invention is believed to represent significant advancements in the art which have substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A device for medializing a paralyzed vocal cord in a larynx, said larynx including an outer layer of thyroid cartilage and a window formed in said thyroid cartilage adjacent to said paralyzed vocal cord, said device comprising:

an anchoring plate having a pair of spaced, threaded apertures formed therein;

a prosthesis member;

a pair of adjustment screws having first and second ends, said adjustment screws being threaded through said threaded apertures, and said first ends of said adjustment screws being rotatably connected to said prosthesis member; and means for securing said anchoring plate over said window in said thyroid cartilage so that said prosthesis member extends through said window and presses against said vocal cord;

said adjustment screws being operable for moving the prosthesis member relative to said anchoring plate and thereby adjusting the medial position of said vocal cord in said larynx.

2. In the device of claim 1, said prosthesis member comprising a wedge shaped body having a first end and a second end, said first ends of said adjustment screws being rotatably connected to said wedge shaped body adjacent the first and second ends thereof.

3. In the device of claim 1, said prosthesis member including a pair of sockets formed therein, said adjustment screw each including a ball element on the first end thereof, said ball elements being received in said sockets to form a ball and socket joint.

4. In the device of claim 1, said prosthesis member comprising a plate element having first and second ends, said first ends of said adjustment screws being rotatably connected to said plate element adjacent the first and second ends thereof.

5. In the device of claim 1, said means for securing comprising a plurality of apertures in said anchoring plate and a plurality of self-tapping screws which are extended through said plurality of apertures and secured to said thyroid cartilage.

6. In the device of claim 1, each of said adjustment screws including a head portion at the second end thereof, said head portions including socket means which are adapted to receive an adjustment tool for rotating said adjustment screws.

7. A device for medializing a paralyzed vocal cord in a larynx, said larynx including an outer layer of thyroid cartilage and a window formed in said thyroid cartilage adjacent to said paralyzed vocal cord, said device comprising:

an anchoring plate having first and second ends, a pair of apertures respectively formed in said plate adjacent to said first and second ends, and a pair of spaced, threaded apertures formed in said plate between said first and second ends;

a prosthesis member;

two adjustment screws having first and second ends, said adjustment screws being threaded through said threaded apertures, and said first ends of said adjustment screws being rotatably connected to the prosthesis member; and a pair of self-tapping screws which are extended through said apertures and secured to said thyroid cartilage, said self-tapping screws being operative for securing said anchoring plate over said window in said thyroid cartilage so that said prosthesis member extends through said window and presses against said vocal cord, said adjustment screws being operative for moving said prosthesis member relative to said anchoring plate and thereby adjusting the medial position of said vocal cord in said larynx.

8. In the device of claim 7, said anchoring plate further including a pair of slots respectively formed therein adjacent said apertures, said device further comprising a second pair of self-tapping screws extending through said slots and secured to said thyroid cartilage.

9. In the device of claim 7, said prosthesis member comprising a wedge shaped body having first and second ends, said first ends of said adjustment screws being rotatably connected to said wedge shaped body adjacent the first and second ends thereof.

10. In the device of claim 7, said prosthesis member including a pair of sockets formed therein, said adjustment screws each including a ball element on the first end thereof, said ball elements being received in said sockets to form a ball and socket joint.

11. In the device of claim 7, said prosthesis member comprising a plate element having first and second ends, said first ends of said adjustment screws being rotatably connected to said plate element adjacent the first and second ends thereof.

12. In the device of claim 11, each of said adjustment screws having a ball element at the first end thereof, and said prosthesis member having a pair of sockets formed therein for receiving said ball elements to form a ball and socket joint.

13. In the device of claim 7, each of said adjustment screws having a head portion at the second end thereof, said head portions including socket means which are adapted to receive an adjustment tool for rotating said adjustment screws.

14. In the device of claim 11, said anchoring plate including a body portion positioned between said first and second ends, said threaded apertures passing through said body portion, and said prosthesis member being positioned adjacent to said body portion.

15. In the device of claim 14, said body portion comprising a rectangular block.

16. In the device of claim 14, said body portion comprising a wedge-shaped block.

17. A device for medializing a paralyzed vocal cord in a larynx, said larynx including an outer layer of thyroid cartilage and a window formed in said thyroid cartilage adjacent to said paralyzed vocal cord, said device comprising:

a body portion having first and second surfaces and first and second ends, and pair of threaded apertures formed in said body portion between said first and second ends;

a first flange member extending outwardly from the first end of said body portion adjacent the first surface thereof;

a second flange member extending outwardly from the second end of said body portion adjacent the second surface thereof;

a prosthesis member; and two adjustment screws having first and second ends, said adjustment screws being threaded through said threaded apertures and said first ends of said adjustment screws being rotatably connected to the prosthesis member; and means for securing said first flange member to said thyroid cartilage so that said body portion and said prosthesis member extend through said window and said prosthesis member presses against said vocal cord, said second flange member being received against an inner surface of said thyroid cartilage, said adjustment screws being operative for moving said prosthesis member relative to said body portion and thereby adjusting the medial position of said vocal cord in said larynx.

18. In the device of claim 17, said means for securing comprising an aperture in said first flange member, and a self-tapping screw extending through said aperture and secured in said thyroid cartilage.

19. In the device of claim 17, said prosthesis member comprising a plate element having first and second ends, said first ends of said adjustment screws being rotatably connected to said plate element adjacent the first and second ends thereof.

20. In the device of claim 17, each of said adjustment screws having a head portion at the second end thereof, said head portions including socket means which are adapted to receive an adjustment tool for rotating said adjustment screws.

* * * * *